(12) United States Patent
Kaminaga et al.

(10) Patent No.: US 11,570,983 B2
(45) Date of Patent: Feb. 7, 2023

(54) CHAMBER FOR TRANSPLANTATION AND DEVICE FOR TRANSPLANTATION

(71) Applicant: FUJIFILM Corporation, Tokyo (JP)

(72) Inventors: Kuniyuki Kaminaga, Ashigarakami-gun (JP); Ryuta Takegami, Ashigarakami-gun (JP); Kazuhiro Hasegawa, Ashigarakami-gun (JP); Yusuke Mochizuki, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 376 days.

(21) Appl. No.: 16/728,456

(22) Filed: Dec. 27, 2019

(65) Prior Publication Data

US 2020/0138014 A1 May 7, 2020

Related U.S. Application Data

(63) Continuation of application No. PCT/JP2018/024668, filed on Jun. 28, 2018.

(30) Foreign Application Priority Data

Jun. 29, 2017 (JP) .............................. JP2017-127657

(51) Int. Cl.
*A01N 1/00* (2006.01)
*A01N 1/02* (2006.01)
*A61B 17/00* (2006.01)

(52) U.S. Cl.
CPC ....................... *A01N 1/0231* (2013.01); *A61B 2017/00969* (2013.01)

(58) Field of Classification Search
None
See application file for complete search history.

(56) References Cited

U.S. PATENT DOCUMENTS

| 5,713,888 A * | 2/1998 | Neuenfeldt .............. A61F 2/022 604/890.1 |
| 2003/0124722 A1 | 7/2003 | Ohgawara et al. |
| 2004/0197374 A1 | 10/2004 | Rezania et al. |
| 2011/0111008 A1 | 5/2011 | Tao et al. |

FOREIGN PATENT DOCUMENTS

| JP | 2003-190259 A | 7/2003 |
| JP | 2004-307505 A | 11/2004 |

(Continued)

OTHER PUBLICATIONS

US 5,808,050 A, 09/1998, Mares-Guia (withdrawn)

(Continued)

*Primary Examiner* — Jyoti Nagpaul
(74) *Attorney, Agent, or Firm* — Birch, Stewart, Kolasch & Birch, LLP

(57) ABSTRACT

According to the present invention, there are provided a chamber for transplantation, as a planar chamber for transplantation which has a structure in which membranes for immunoisolation face each other, and which is capable of stably enclosing a biological constituent, including a membrane for immunoisolation at a boundary between an inside and an outside of the chamber for transplantation, in which the membranes for immunoisolation which face each other have joint portions that are joined to each other, an interior space includes a point at a distance of 10 mm or longer from any position of the joint portion, and the membrane for immunoisolation has flexibility that allows a distance of 1 mm to 13 mm as the following distance: in a case where a portion of 10 mm from a side surface of one short side of a 10 mm×30 mm rectangular test piece of the membrane for immunoisolation is vertically sandwiched between flat plates, and the flat plates are placed horizontally, a distance between a horizontal plane including a center plane in a thickness direction of the sandwiched portion of the mem- (Continued)

brane for immunoisolation, and a part, which is farthest from the horizontal plane, of a residual 20 mm-portion projecting from the flat plate; and a device for transplantation including the chamber for transplantation enclosing a biological constituent therein.

9 Claims, 2 Drawing Sheets

(56) References Cited

FOREIGN PATENT DOCUMENTS

| | | |
|---|---|---|
| JP | 2013-507373 A | 3/2013 |
| WO | WO 2017/023379 A1 | 2/2017 |

OTHER PUBLICATIONS

International Preliminary Report on Patentability and Written Opinion of the International Searching Authority (Forms PCT/IB/326, PCT/IB/373 and PCT/ISA/237), dated Jan. 9, 2020, for International Application No. PCT/JP2018/024666, with an English Translation.

International Search Report (PCT/ISA/210), dated Sep. 18, 2018, for International Application No. PCT/JP2018/024668, with an English translation.

Tatarkiewicz et al., "Reversal of Hyperglycemia in Mice After Subcutaneous Transplantation of Macroencapsulated Islets", URL: https://journals.lww.com/transplantjournal/Fulltext/1999/03150/REVERSAL_OR_HYPERGLYCEMIA_IN_M Dec. 16, 2019 pp. 1-10 (10 pages).

* cited by examiner

CHAMBER FOR TRANSPLANTATION AND DEVICE FOR TRANSPLANTATION

CROSS-REFERENCE TO RELATED APPLICATIONS

This application is a continuation of PCT International Application No. PCT/JP2018/024668 filed on Jun. 28, 2018, which claims priority under 35 U.S.C § 119 (a) to Japanese Patent Application No. 2017-127657 filed on Jun. 29, 2017, the entire content of which is incorporated herein by reference.

BACKGROUND OF THE INVENTION

1. Field of the Invention

The present invention relates to a chamber for transplantation which includes a membrane for immunoisolation, and a device for transplantation which includes the chamber for transplantation.

2. Description of the Related Art

Immunoisolation is one of methods for preventing immune reactions in a recipient during transplantation of biological constituents such as cells, tissues, or organs. A membrane for immunoisolation is a selectively permeable membrane which allows water, oxygen, glucose, or the like to permeate, and which, at the same time, performs immunoisolation by inhibiting permeation of immune cells and the like involved in an immune rejection. For example, while preventing an immune rejection, it is possible to achieve a purpose of transplantation by a device for transplantation utilizing a membrane for immunoisolation which allows physiologically active substances to permeate therethrough, for transplantation of cells secreting the physiologically active substances.

Transplantation, 67, 665 (1999) discloses that transplantation is performed using a commercially available chamber for transplantation (TheraCyte (registered trade name)), the chamber being formed by using a porous membrane that is a laminate membrane obtained by laminating a membrane having a pore diameter of 0.45 µm and cell retention properties and an outer membrane of polytetrafluoroethylene (PTFE) having a pore diameter of 5 µm.

SUMMARY OF THE INVENTION

Many chambers for transplantation which are currently under development are designed to be planar and thin like the chamber for transplantation disclosed in Transplantation, 67, 665 (1999). The reason for this is that a distance between a membrane for immunoisolation and enclosed cells needs to be kept short to deliver nutrients to the cells enclosed in a chamber for transplantation. However, there is a problem of a tendency of collapse of a shape of an interior space in a case of increasing an area of a chamber for transplantation in which membranes for immunoisolation face each other to form a planar interior space.

An object of the present invention is to provide a planar chamber for transplantation which has a structure in which membranes for immunoisolation face each other, and which can stably enclose a biological constituent. Another object of the present invention is to provide a device for transplantation which can stably enclose a biological constituent.

The inventors of the present invention have conducted intensive studies to achieve the above-mentioned objects, have found that an adjustment of flexibility of a membrane for immunoisolation can provide a chamber for transplantation in which a shape of an interior space is less likely to collapse, and therefore have completed the present invention based on these findings.

That is, the present invention provides the following <1> to <12>.

<1> A chamber for transplantation, comprising:
a membrane for immunoisolation at a boundary between an inside and an outside of the chamber for transplantation,
in which the membranes for immunoisolation face each other to form an interior space,
the membranes for immunoisolation which face each other have joint portions that are joined to each other,
the interior space includes a point at a distance of 10 mm or longer from any position of the joint portion, and
the membrane for immunoisolation has flexibility that allows a distance of 1 mm to 13 mm as the following distance:
in a case where a portion of 10 mm from a side surface of one short side of a 10 mm×30 mm rectangular test piece of the membrane for immunoisolation is vertically sandwiched between flat plates, and the flat plates are placed horizontally, a distance between a horizontal plane including a center plane in a thickness direction of the sandwiched portion of the membrane for immunoisolation, and a part, which is farthest from the horizontal plane, of a residual 20 mm-portion projecting from the flat plate.

<2> The chamber for transplantation according to <1>, in which a maximum cross-sectional area of the interior space is 4 cm$^2$ to 200 cm$^2$.

<3> The chamber for transplantation according to <1> or <2>, in which the joint portions are at end portions of the membranes for immunoisolation which face each other.

<4> The chamber for transplantation according to <1> or <2>, in which the joint portions are only at end portions of the membranes for immunoisolation which face each other.

<5> The chamber for transplantation according to any one of <1> to <4>, in which the membrane for immunoisolation includes a porous membrane containing a polymer.

<6> The chamber for transplantation according to any one of <1> to <4>, in which the membrane for immunoisolation is formed of a porous membrane containing a polymer.

<7> The chamber for transplantation according to <5> or <6>, in which a thickness of the porous membrane is 25 µm to 250 µm.

<8> The chamber for transplantation according to any one of <5> to <7>, in which a porosity of the porous membrane is 35% to 90%.

<9> The chamber for transplantation according to any one of <5> to <8>, in which the porous membrane contains polysulfone or polyethersulfone.

<10> A device for transplantation, comprising the chamber for transplantation according to any one of <1> to <9> enclosing a biological constituent therein.

<11> The device for transplantation according to <10>, in which the biological constituent releases a physiologically active substance.

<12> The device for transplantation according to <11>, in which the physiologically active substance is insulin.

According to the present invention, it is possible to provide a planar chamber for transplantation which has a structure in which membranes for immunoisolation face each other, and which can stably enclose a biological constituent; and a device for transplantation which can stably enclose a biological constituent.

DESCRIPTION OF THE PREFERRED EMBODIMENTS

Figure 1:
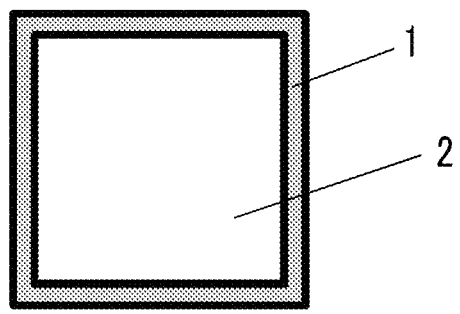
FIG. 1 is a view showing a joint portion in chambers for transplantation of Examples 1 to 10 and Comparative Examples 1 and 2.

Hereinafter, the present invention will be described in detail.

In the present specification, "to" is used to refer to a meaning including numerical values denoted before and after "to" as a lower limit value and an upper limit value.

<<Chamber for Transplantation>>

A chamber for transplantation is a container for transplanting a biological constituent into a recipient. The chamber for transplantation can enclose the biological constituent therein.

The chamber for transplantation according to the embodiment of the present invention includes a membrane for immunoisolation at a boundary between an inside and an outside of the chamber for transplantation. By disposing the membrane for immunoisolation in such a manner, it is possible to protect the biological constituent enclosed in the chamber for transplantation from immune cells and the like present outside, and to introduce nutrients such as water, oxygen, and glucose into the inside of the chamber for transplantation from the outside.

The membrane for immunoisolation may be disposed on the entire surface of the boundary between the inside and the outside (boundary separating the inside from the outside) of the chamber for transplantation or may be disposed on a part of the surface, but it is preferably disposed on the entire surface in terms of practicalities.

In a case where the membrane for immunoisolation is not disposed on the entire surface of the boundary between the inside and the outside of the chamber for transplantation, it is sufficient for a residual surface to be formed of an impermeable membrane not allowing permeation of nutrients such as oxygen, water, and glucose, in addition to cells and the like.

In the chamber for transplantation according to the embodiment of the present invention, the membranes for immunoisolation face each other to form an interior space. In other words, the chamber for transplantation according to the embodiment of the present invention has an interior space between the membranes for immunoisolation which face each other. It is preferable that all regions of the interior space be present between the membranes for immunoisolation which face each other.

As the membranes for immunoisolation, for example, two membranes for immunoisolation may face each other, or portions of one membrane for immunoisolation may face each other by folding the one membrane for immunoisolation with a line-symmetric structure into two. In a case where two membranes for immunoisolation are used as the membranes for immunoisolation which face each other, both may be the same membrane or different membranes, but they are preferably the same membrane.

The chamber for transplantation according to the embodiment of the present invention has a joint portion at which the membranes for immunoisolation which face each other are joined to each other. The membranes for immunoisolation which face each other are joined at a part thereof.

A portion of the membrane for immunoisolation that is being joined is not particularly limited, but is preferably an end portion of the membrane for immunoisolation. In particular, it is preferable that end portions be joined to each other. In the present specification, in a case where the term "end portion" is used regarding the membrane, it means a peripheral portion or a part thereof having a constant width which is substantially in contact with the side surface (edge) of the membrane thickness. It is preferable that all of outer peripheries except an injection port and the like to be described later be joined to each other between the membranes for immunoisolation.

The chamber for transplantation according to the embodiment of the present invention may further have a joint portion in the interior space formed by joining the end portions as described above. Such a joint portion can be provided to assist in, for example, maintaining a shape of the interior space and homogeneously distributing an enclosed biological constituent.

At the joint portion, the membranes for immunoisolation may be adhered or fusion welded to each other.

For example, the membranes for immunoisolation at the joint portion can be adhered to each other using a curable adhesive. Examples of adhesives include known adhesives such as epoxy-based adhesives, silicone-based adhesives, acrylic-based adhesives, and urethane-based adhesives.

In addition, a thermoplastic resin may be sandwiched between the membranes for immunoisolation, that is between porous membranes, the portion may be heated, and thereby the membranes for immunoisolation may be joined to each other. In this case, as the thermoplastic resin, a resin having a melting point lower than that of the polymer forming the porous membrane is preferably used. Specific examples of thermoplastic resins include polyethylene, polypropylene, polyurethane, polyvinyl chloride, polytetrafluoroethylene, polyethylene terephthalate, and polycarbonate. Among them, polyethylene, polypropylene, polyurethane, polyvinyl chloride, and polytetrafluoroethylene are preferable, and polyethylene, polyurethane, and polyvinyl chloride are more preferable.

Furthermore, the porous membranes in the membrane for immunoisolation may be fusion welded to each other in a state of coming in direct contact with each other by not sandwiching another material therebetween. By such fusion welding, it is possible to obtain a chamber for transplantation not having a problem derived from a resin sandwiched between the porous membranes or the like. In a case where porous membranes which contain a polymer selected from the group consisting of polysulfone and polyethersulfone is used, the porous membranes can be fusion welded and integrated by heating at a temperature of a glass transition temperature or higher of the polymer and lower than a melting point of the polymer. Specifically, the heating for the fusion welding may be performed at a temperature of 190° C. or higher and lower than 340° C. and is preferably performed at a temperature of 230° C. or higher and lower than 340° C.

The interior space is a space for maintaining the biological constituent. In the chamber for transplantation according to the embodiment of the present invention, the interior space includes a point at a distance of 10 mm or longer from any position of the joint portion. In other words, in the interior space, there is a point at a distance of 10 mm or longer from any position of the joint portion. As described above, as a point becomes farther from the joint portion in the interior space, it becomes more difficult to maintain the shape of the interior space. However, in the chamber for transplantation according to the embodiment of the present invention, by using a membrane for immunoisolation having flexibility to be described later, it is possible to maintain a distance between the membranes for immunoisolation which face each other, thereby maintaining the shape of the interior space. In the chamber for transplantation according to the embodiment of the present invention, the interior space may include a point at a distance of 15 mm or longer, a point at a distance of 20 mm or longer, a point at a distance of 30 mm or longer, or a point at a distance of 40 mm or longer from any position of the joint portion.

In addition, even in a case where the maximum cross-sectional area of the interior space of the chamber for transplantation according to the embodiment of the present invention is 4 cm$^2$ or more or 10 cm$^2$ or more, by using a membrane for immunoisolation having flexibility to be described later, it is possible to maintain a distance between the membranes for immunoisolation which face each other, thereby maintaining the shape of the interior space. The maximum cross-sectional area can be obtained from an image of computed tomography. The maximum cross-sectional area of the interior space of the chamber for transplantation is preferably 200 cm$^2$ or less, and is more preferably 100 cm$^2$ or less.

A chamber for transplantation having a larger maximum cross-sectional area can be provided by incorporating a partition into the interior space. The reason for this is that, in the chamber for transplantation in which the membranes for immunoisolation face each other to form a planar interior space, the partition can function as a support for maintaining a distance between the membranes for immunoisolation. In such a chamber for transplantation having the partition, a point at a distance of 10 mm or longer from any position of the joint portion of the partition may be present as a point at a distance of 10 mm or longer from any position.

The partition may be formed of, for example, a biocompatible resin and the like. In addition, the partition may be provided as the joint portion. Regarding a position or the like of the partition in the interior space, the description of JP1996-502667A (JP-H08-502667A) can be referred to.

A shape of the chamber for transplantation may be a shape such as a pouched-like shape, a bag shape, a tube shape, or a microcapsule shape. A shape of the chamber for transplantation is preferably a shape capable of preventing movement of the chamber for transplantation within a recipient in a case where the chamber for transplantation is used as a device for transplantation to be described later. Specific examples of shapes of the chamber for transplantation include a cylindrical shape, a disk-like shape, a rectangular shape, an egg shape, a star shape, a circular shape, and the like. The chamber for transplantation preferably has a shape of sheet.

Figure 3:
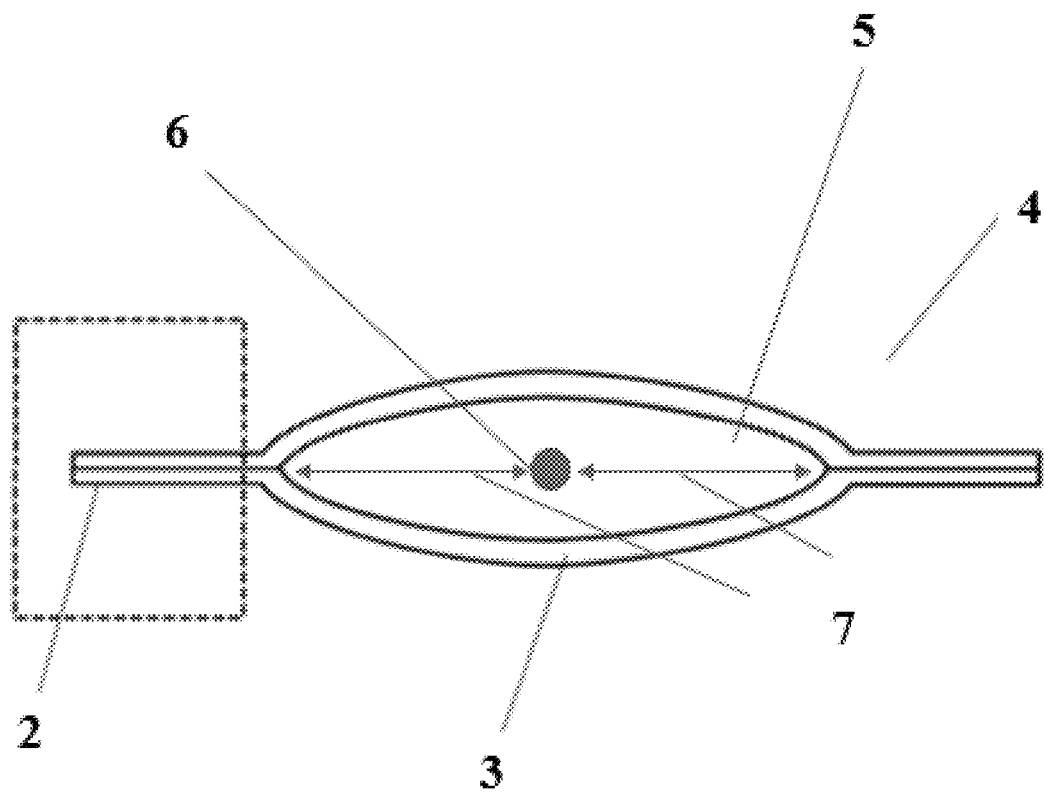
FIG. 3 illustrates one embodiment of a chamber for transplantation of the present invention.

In summary, and as illustrated in FIG. 3, a chamber for transplantation 4 comprises a membrane for immunoisolation 3 at a boundary between an inside and an outside of the chamber for transplantation 4, in which the membranes for immunoisolation 3 face each other to form an interior space 5. The membranes for immunoisolation 3, which face each other, have joint portions 2 that are joined to each other. The interior space 5 includes a point 6 at a distance 7 of 10 mm or longer from any position of the joint portion 2.

<Membrane for immunoisolation>

[Flexibility]

Figure 4:
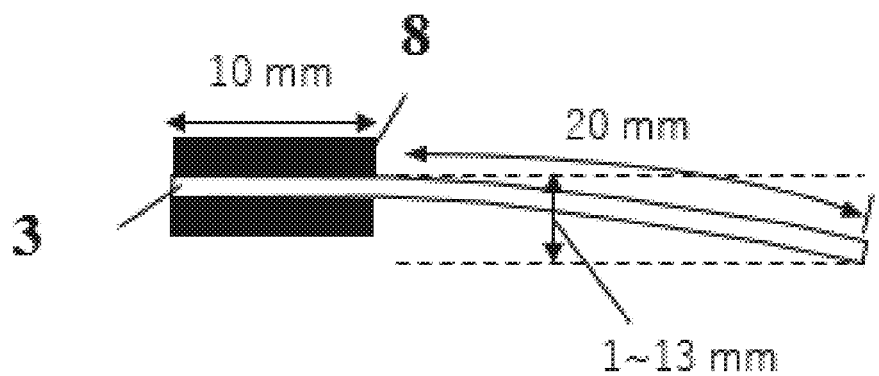
FIG. 4 illustrates a method for measuring the flexibility of a membrane for immunoisolation.

In the chamber for transplantation according to the embodiment of the present invention, any of the membranes for immunoisolation which face each other as described above has a predetermined flexibility. The flexibility can be confirmed by the following method with reference to the method described in paragraph 0018 of JP2017-052113A and as illustrated in FIG. 4. For confirmation of the flexibility, a 10 mm×30 mm rectangular test piece of the membrane for immunoisolation 3 is prepared. A portion of 10 mm from a side surface of one short side of this rectangular test piece is vertically sandwiched between flat plates 8, and the flat plates 8 are placed horizontally. In this case, the flexibility is determined by displacement of an unsandwiched portion of the membrane for immunoisolation 3 in a gravity direction. The membrane for immunoisolation 3 used in the chamber for transplantation according to the embodiment of the present invention has flexibility that allows a distance between a horizontal plane including a center plane in a thickness direction of the sandwiched portion of the membrane for immunoisolation 3, and a part, which is farthest from the horizontal plane, of a residual 20 mm-portion projecting from the flat plate 8, to be 1 mm to 13 mm. It is preferable that the distance be 5 mm to 10 mm. Evaluation of the flexibility is performed at a temperature of 25° C. and a relative humidity of 60%. In addition, the evaluation is performed on a chamber for transplantation in a dry state.

The flexibility of the membrane for immunoisolation can be adjusted by a material, thickness, pore diameter of the porous membrane (bubble point diameter), porosity of the porous membrane, and the like.

[Other Properties]

A membrane for immunoisolation refers to a membrane used for immunoisolation.

Immunoisolation is one of a method for preventing an immune rejection by a recipient in a case of transplantation. Here, the immune rejection is a rejection by a recipient with respect to a biological constituent to be transplanted. A biological constituent is isolated from an immune rejection by a recipient due to immunoisolation. Examples of immune rejections include reactions based on cellular immune responses and reactions based on humoral immune responses.

The membrane for immunoisolation is a selectively permeable membrane that allows nutrients such as oxygen, water, and glucose to permeate therethrough, and inhibits permeation of immune cells and the like involved in an immune rejection. Examples of immune cells include macrophages, dendritic cells, neutrophils, eosinophils, basophils, natural killer cells, various T cells, B cells, and other lymphocytes.

Depending on the application, the membrane for immunoisolation preferably inhibits permeation of high-molecular-weight proteins such as immunoglobulins (IgM, IgG, and the like) and complements, and preferably allows a relatively low-molecular-weight physiologically active substances such as insulin to permeate therethrough.

The selective permeability of the membrane for immunoisolation may be adjusted according to the application. The membrane for immunoisolation may be a selectively permeable membrane which blocks a substance having a molecular weight such as 500 kDa or more, 100 kDa or more, 80 kDa or more, or 50 kDa or more. For example, it is preferable that the membrane for immunoisolation be capable of inhibiting permeation of the smallest IgG (molecular weight of about 160 kDa) among antibodies. In addition, the membrane for immunoisolation may be a selectively permeable membrane which blocks a substance having a diameter such as 500 nm or more, 100 nm or more, 50 nm or more, or 10 nm or more, as a sphere size.

The membrane for immunoisolation preferably includes a porous membrane. The membrane for immunoisolation may be formed of only the porous membrane or may contain other layers such as a hydrogel membrane. The membrane for immunoisolation preferably has the porous membrane at least one surface thereof, and it is also preferable that the membrane for immunoisolation be formed of the porous membrane.

A thickness of the membrane for immunoisolation is not particularly limited, but may be 25 μm to 500 μm, is preferably 30 μm to 300 μm, and is more preferably 35 μm to 250 μm.

[Porous Membrane]
(Structure of Porous Membrane)

The membrane for immunoisolation preferably includes a porous membrane. The porous membrane is a membrane having a plurality of pores. Pores can be confirmed by, for example, captured images of a scanning electron microscope (SEM) or captured images of a transmission electron microscope (TEM) of a cross section of the membrane.

A thickness of the porous membrane is not particularly limited, but may be 25 μm to 250 μm, is preferably 30 μm to 220 μm, and is more preferably 35 μm to 200 μm.

A porosity of the porous membrane varies depending on polymers used and a thickness of the porous membrane, but it is preferably 35% to 90%. For example, in a case of using polysulfone as a polymer, a porosity is preferably 75% to 85%. Within such a range, semi-permeability necessary for immunoisolation can be imparted. In addition, by adjusting the porosity together with the thickness, the flexibility of the porous membrane can be adjusted.

A porosity can be obtained based on the following formula.

Porosity (%)[1−{m/ρ/(S×d)}]×100 m: Mass of porous membrane (g)
ρ: Polymer density (g/cm$^3$)
S: Area of porous membrane (cm$^2$)
d: Thickness of porous membrane (cm)

After sufficiently freeze-pulverizing the porous membrane, the polymer density thereof can be obtained by B method of JIS K7112 (1999).

A bubble point diameter of the porous membrane is preferably 0.02 μm to 25 μm, is more preferably 0.2 μm to 10 μm, and is even more preferably 0.5 μm to 5 μm. The bubble point is measured using a measurement method of immersing the porous membrane in a liquid, and utilizing bubbles first generated from a pore with the maximum pore diameter in a neck portion when an air pressure is increased from a lower side and reaches a certain value. The pressure at this time is referred to as a bubble point pressure, and a bubble point diameter can be obtained using a known formula based on the bubble point pressure. In a porous membrane not having pore diameter distribution in the thickness direction, a bubble point diameter usually corresponds to the maximum pore diameter of the porous membrane. In a porous membrane having pore diameter distribution in the thickness direction, a bubble point diameter corresponds to the maximum pore diameter of a compact portion to be described later.

The minimum pore diameter of the porous membrane is preferably 0.02 μm to 1.5 μm, and is more preferably 0.02 μm to 1.3 μm. The reason is that the minimum pore diameter of such a porous membrane can inhibit permeation of at least normal cells. Here, the minimum pore diameter of the porous membrane can be measured by ASTM F316-80.

(Porous Membrane Having Pore Diameter Distribution in Thickness Direction)

It is preferable that the porous membrane have pore diameter distribution in the thickness direction. In addition, the porous membrane preferably has a layered compact portion where a pore diameter is smallest within the membrane. Furthermore, it is preferable that a pore diameter continuously increase in the thickness direction from the compact portion toward at least one of surfaces of the porous membrane. The pore diameter is determined by an average pore diameter of a parting line which will be described later.

The surface of the membrane means a main surface (a front surface or a back surface showing an area of the membrane), and does not mean a surface in the thickness direction of an end of the membrane. The surface of the porous membrane may be an interface with another layer. It is preferable that the porous membrane have the same structure in an intra-membrane direction (a direction parallel to the membrane surface) with respect to pore diameters or pore diameter distribution (a difference in pore diameters in the thickness direction).

By using the porous membrane having pore diameter distribution in the thickness direction, the life of the chamber for transplantation can be improved. The reason is that, by using a plurality of membranes having substantially different pore diameters, effects are obtained as though multistage filtration would be carried out, and therefore a deterioration in the membrane can be prevented.

A pore diameter may be measured from a photograph of a cross section of the membrane obtained by an electron microscope. The porous membrane can be cut with a microtome or the like, and it is possible to obtain a photograph of a cross section of the porous membrane as a section of a thin membrane which a cross section can be observed.

In the present specification, the comparison of pore diameters in the thickness direction of the membrane is performed by comparing pore diameters in 19 parting lines in a case where an SEM image of the cross section of the membrane is divided into 20 in the thickness direction of the membrane. 50 or more consecutive pores that intersect or are in contact with the parting line are selected, each of the pore diameters is measured, and an average value is calculated as an average pore diameter. Here, as the pore diameter, not a length of a portion where the selected pore intersects the parting line, but a diameter is used, the diameter being calculated using an area, which is obtained by calculating an area of pores calculated from an SEM image of the cross section of the membrane by image processing, as an area of a true circle. In this case, for a parting line in which pores are large and therefore only up to 50 pores can be selected, an average pore diameter is assumed to an average pore diameter obtained by measuring 50 pores by broadening the field of view of an SEM image for obtaining the cross section of the membrane. Pore diameters in the thickness direction of the membrane are compared by comparing the obtained average pore diameter for each parting line.

The layered compact portion having the smallest pore diameter refers to a layered portion of the porous membrane including the parting line where an average pore diameter becomes smallest among parting lines in a photograph of the cross section of the membrane. The compact portion may include two or more parting lines. For example, in a case where two or more parting lines, which have an average pore diameter 1.1 times or less the minimum average pore diameter, are consecutive, the compact portion is assumed to include two or more consecutive parting lines. In the present specification, a thickness of the compact portion is a product of the number of parting lines included in the compact portion and one-twentieth of the thickness of the membrane.

In the porous membrane having pore diameter distribution in the thickness direction, an average pore diameter of the compact portion can be determined as the minimum average pore diameter of the porous membrane. It is preferable that the minimum pore diameter be measured by ASTM F316-80 after determining the compact portion.

It is preferable that the porous membrane having pore diameter distribution in the thickness direction have the compact portion within the membrane. The phrase "within the membrane" means that the compact portion is not in contact with the surface of the membrane. The phrase "having the compact portion within the membrane" means that the compact portion is not the closest section to any surface of the membrane. By using the porous membrane having a structure having the compact portion within the membrane, permeability of a substance intended to permeate therethrough is unlikely to be diminished as compared to a case of using a porous membrane having the same compact portion in contact with the surface thereof. Although not bound by any theory, it is perceived that protein adsorption is less likely to occur due to the presence of the compact portion within the membrane.

It is preferable that the compact portion be biased to one of the front surface side than a central portion in thickness of the porous membrane. Specifically, the compact portion is preferably located between any one surface of the porous membrane and a portion at a distance of less than half the thickness of the porous membrane from the surface, and it is even more preferably located between any one surface of the porous membrane and a portion at a distance of two-fifths the of the porous membrane from the surface. This distance may be determined from the photograph of the cross section of the membrane described above. In the present specification, the surface of the porous membrane closer to the compact portion is referred to as a "surface X." In a case where the porous membrane has the compact portion and the surface X, it is preferable in the chamber for transplantation that the surface X of the porous membrane be on the inside thereof. That is, it is preferable that the membrane for immunoisolation be disposed so that the compact portion of the porous membrane in the membrane for immunoisolation is closer to the inside of the chamber for transplantation. By setting the surface X in the inside of the chamber for transplantation, it is possible to make permeability of physiologically active substances higher.

In the porous membrane having pore diameter distribution in the thickness direction, it is preferable that the pore diameter continuously increase in the thickness direction from the compact portion toward at least one of the surfaces. In the porous membrane, the pore diameter may continuously increase in the thickness direction toward the surface X from the compact portion, the pore diameter may continuously increase in the thickness direction toward the surface opposite to the surface X from the compact portion, and the pore diameter may continuously increase in the thickness direction toward any surface of the porous membrane from the compact portion. Among them, it is preferable that the pore diameter continuously increase in the thickness direction toward at least the surface opposite to the surface X from the compact portion, and it is preferable that the pore diameter continuously increase in the thickness direction toward any surface of the porous membrane from the compact portion. The sentence "the pore diameter continuously increases in the thickness direction" means that a difference in average pore diameters between sections adjacent to each other in the thickness direction increases by 50% or less, preferably increases by 40% or less, and more preferably increases by 30% or less of a difference between the maximum average pore diameter and the minimum average pore diameter. The phrase "continuously increasing" essentially means that a pore diameter increases uniformly without decreasing, but a decreasing portion may occur accidentally. For example, in a case of combining two sections from the surface, in a case where an average value of a combination increases uniformly (uniformly decreases toward the compact portion from the surface), it can be determined that "the pore diameter continuously increases in the thickness direction toward the surface of the membrane from the compact portion."

The porous membrane having pore diameter distribution in the thickness direction can be realized by, for example, a manufacturing method to be described later. It is particularly preferable that the porous membrane having pore diameter distribution in the thickness direction be manufactured using a polymer selected from the group consisting of polysulfone and polyethersulfone.

In the porous membrane having pore diameter distribution in the thickness direction, an average pore diameter of a parting line having the maximum average pore diameter among the parting lines can be determined as the maximum average pore diameter of the porous membrane. A maximum average pore diameter of the porous membrane having pore diameter distribution in the thickness direction is preferably 0.15 µm to 100 µm, is more preferably 1.0 µm to 50 µm, and is even more preferably 2.0 µm to 21 µm. It is preferable that the parting line where an average pore diameter becomes maximum be a parting line closest to any surface of the porous membrane.

In the porous membrane having pore diameter distribution in the thickness direction, a ratio of an average pore diameter (minimum average pore diameter) to the maximum average pore diameter of the compact portion (also referred to as an "anisotropy ratio" in the present specification, which is a ratio of the minimum average pore diameter to the maximum average pore diameter of the porous membrane, and is a value obtained by dividing the maximum average pore diameter by the minimum average pore diameter) is preferably 3 or more, is more preferably 4 or more, and is even more preferably 5 or more. The reason is that an average pore diameter except for that of the compact portion increases to increase substance permeability of the porous membrane. In addition, the anisotropy ratio is preferably 25 or less and is more preferably 20 or less. The reason is that effects, as though multistage filtration would be carried out, can be efficiently obtained within a range where an anisotropy ratio is 25 or less.

(Elemental Distribution of Porous Membrane)

Formulas (I) and (II) are preferably satisfied for at least one surface of the porous membrane.

$$B/A \leq 0.7 \tag{I}$$

$$A \geq 0.015 \tag{II}$$

In the formula, A represents a ratio of an N element (nitrogen atom) to a C element (carbon atom) on a surface of the membrane, and B represents a ratio of the N element to the C element at a depth of 30 nm from the same surface.

Formula (II) shows that a certain amount or more of N element is present on at least one surface of the porous membrane, and Formula (I) shows that an N element in the porous membrane is localized at a depth of less than 30 nm of the surface.

With the surface satisfying Formulas (I) and (II), a bioaffinity of the porous membrane, particularly, a bioaffinity of the surface side satisfying Formulas (I) and (II) becomes high.

In the porous membrane, either one of surfaces may satisfy Formulas (I) and (II), or both surfaces may satisfy Formulas (I) and (II), but it is preferable that both surfaces satisfy Formulas (I) and (II). In a case where either one of surfaces satisfies Formulas (I) and (II), the surface thereof may be in an inside or an outside of a chamber for transplantation to be described later, but the surface is preferably in the inside thereof. In addition, in a case where only one of any surface satisfies Formulas (I) and (II) and the porous membrane has the above-mentioned surface X, a surface satisfying Formulas (I) and (II) is preferably the surface X.

In the present specification, a ratio (A value) of N element to C element on the membrane surface and a ratio (B value) of N element to C element at a depth of 30 nm from the surface are obtained by calculating using XPS measurement results. The XPS measurement is X-ray photoelectron spectroscopy, which is a method for irradiating a membrane surface with X-rays, measuring kinetic energy of photoelectrons emitted from the membrane surface, and analyzing a composition of elements constituting the membrane surface. Under conditions using a monochromated Al-Kα ray described in Examples, the A value is calculated from results at the start of sputtering, and the B value is calculated from time results, which are calculated that the ray is at 30 nm from the surface of the membrane measured from a sputtering rate.

B/A may be 0.02 or more, and is preferably 0.03 or more, and is more preferably 0.05 or more.

A is preferably 0.050 or more and is more preferably 0.080 or more. In addition, A may be 0.20 or less, and is preferably 0.15 or less, and is more preferably 0.10 or less.

B may be 0.001 to 0.10, and is preferably 0.002 to 0.08, and is more preferably 0.003 to 0.07.

In a method for manufacturing the porous membrane which will be described later, the elemental distribution of the porous membrane, especially the distribution of an N element, can be controlled by a moisture concentration contained in the temperature-controlled humid air, a time to apply the temperature-controlled humid air, a temperature of a coagulation liquid, an immersion time, a temperature of a diethylene glycol bath for washing, an immersion time in the diethylene glycol bath for washing, a speed of a porous membrane manufacture line, and the like. The distribution of the N element can also be controlled by an amount of moisture contained in a stock solution for forming a membrane.

(Composition of Porous Membrane)

The porous membrane may contain a polymer. It is preferable that the porous membrane be essentially composed of a polymer.

The polymer forming the porous membrane is preferably biocompatible. Here, the term "biocompatible" means that the polymer has non-toxic and non-allergenic properties, but does not have properties such that the polymer is encapsulated in a living body.

The number average molecular weight (Mn) of the polymer is preferably 1,000 to 10,000,000, and is more preferably 5,000 to 1,000,000.

Examples of polymers include thermoplastic or thermosetting polymers. Specific examples of polymers include polysulfone, cellulose acylate such as cellulose acetate, nitrocellulose, sulfonated polysulfone, polyethersulfone, polyvinylidene fluoride, polyacrylonitrile, styrene-acrylonitrile copolymer, styrene-butadiene copolymer, saponified ethylene-vinyl acetate copolymer, polyvinyl alcohol, polycarbonate, an organosiloxane-polycarbonate copolymer, a polyester carbonate, an organopolysiloxane, a polyphenylene oxide, a polyamide, a polyimide, polyamideimide, polybenzimidazole, ethylene vinyl alcohol copolymer, polytetrafluoroethylene (PTFE), and the like. From the viewpoints of solubility, optical physical properties, electrical physical properties, strength, elasticity, and the like, polymers may be homopolymers, copolymers, polymer blends, or polymer alloys.

Among them, polysulfone, polyethersulfone, cellulose acylate, and polyvinylidene fluoride are preferable, and polysulfone is more preferable.

In a case where polysulfone or polyethersulfone is used as the polymer, the porous membrane preferably further contains a hydrophilic polymer. Examples of hydrophilic polymers include polyvinylpyrrolidone, hydroxypropyl cellulose, hydroxyethyl cellulose, and the like. Among them, polyvinylpyrrolidone is preferable. By combining polysulfone or polyethersulfone which are hydrophobic with the hydrophilic polymer, biocompatibility can be improved.

The porous membrane may contain other components other than the above-mentioned components as an additive.

Examples of additives include metal salts of inorganic acids such as sodium chloride, lithium chloride, sodium nitrate, potassium nitrate, sodium sulfate, and zinc chloride; metal salts of organic acids such as sodium acetate and sodium formate; other polymers such as polyethylene glycol; high polymer electrolytes such as sodium polystyrene sulfonate and polyvinyl benzyl trimethyl ammonium chloride; ionic surfactants such as sodium dioctyl sulfosuccinate and sodium alkyl sodium taurate; and the like. The additive may act as a swelling agent for a porous structure. As an additive, it is preferable to use a metal salt. The porous membrane containing polysulfone or polyethersulfone preferably contains lithium chloride.

The porous membrane is preferably a membrane formed from a single composition as a single layer, and preferably not has a laminated structure of a plurality of layers. By forming the porous membrane from one composition as a single layer, it is possible to manufacture the chamber for transplantation at low costs by a simple procedure.

(Method for Manufacturing Porous Membrane)

A method for manufacturing the porous membrane is not particularly limited as long as the method can form the porous membrane having the above-mentioned structure, and any general methods for forming a polymer membrane can be used. Examples of methods for forming a polymer membrane include a stretching method, a flow-casting method, and the like, and a flow-casting method is preferable. In the flow-casting method, the stock solution for forming a membrane which contains a polymer is flow-cast on a support. By selecting a solvent and an additive contained together with the polymer in the stock solution for forming a membrane, a desired porosity can be imparted to the manufactured membrane, or a pore diameter thereof can be adjusted. In addition, by adjusting an amount of stock solution for forming a membrane which is for flow casting or a drying method thereof, a thickness, pore diameter, porosity, and the like can be changed, and thereby flexibility is adjusted.

As the support, a plastic film or a glass plate may be used. Examples of materials of the plastic film include polyester such as polyethylene terephthalate (PET), polycarbonate, acrylic resin, epoxy resin, polyurethane, polyamide, polyolefin, a cellulose derivative, silicone, and the like. As the support, a glass plate or PET is preferable, and PET is more preferable.

The stock solution for forming a membrane may contain a solvent. A solvent having high solubility of the polymer to be used (hereinafter referred to as "favorable solvent") may be used depending on a polymer to be used. In a case of using a coagulation liquid to be described later in the manufacturing of the porous membrane, a favorable solvent is a solvent quickly substituted with the coagulation liquid in a case where the membrane is immersed in the coagulation liquid. Examples of solvents include N-methyl-2-pyrrolidone, dioxane, tetrahydrofuran, dimethylformamide, dimethylacetamide, or a mixed solvent thereof in a case where the polymer is polysulfone and the like; dioxane, N-methyl-2-pyrrolidone, dimethylformamide, dimethylacetamide, dimethylsulfoxide, or a mixed solvent thereof in a case where the polymer is polyacrylonitrile and the like; dimethylformamide, dimethylacetamide, or a mixed solvent thereof in a case where the polymer is polyamide and the like; acetone, dioxane, tetrahydrofuran, N-methyl-2-pyrrolidone, or a mixed solvent thereof in a case where the polymer is cellulose acetate and the like. Among them, N-methyl-2-pyrrolidone is preferably used.

In addition to a favorable solvent, the stock solution for forming a membrane preferably use a solvent (hereinafter referred to as "non-solvent") in which the solubility of the polymer is low but is compatible with the solvent of the polymer. Examples of non-solvents include water, cellosolves, methanol, ethanol, propanol, acetone, tetrahydrofuran, polyethylene glycol, glycerin, and the like. Among these, it is preferable to use water.

A concentration of the polymer as the stock solution for forming a membrane may be 5 mass % to 35 mass %, is preferably 10 mass % to 30 mass %. By setting the concentration thereof to 35 mass % or less, sufficient permeability (for example, water permeability) can be imparted to the obtained porous membrane. By setting the concentration thereof to 5 mass % or more, the formation of a porous membrane which selectively allows substances to permeate can be secured. An amount of additive to be added is not particularly limited as long as the homogeneity of the stock solution for forming a membrane is not lost by the addition, but is 0.5% by volume to 10% by volume respect to a general solvent. In a case where the stock solution for forming a membrane contains a non-solvent and a favorable solvent, a ratio of the non-solvent to the favorable solvent is not particularly limited as long as a mixed solution can be maintained in a homogeneous state, but is preferably 1.0 mass % to 50 mass %, is more preferably 2.0 mass % to 30 mass %, and is even more preferably 3.0 mass % to 10 mass %.

It is possible to produce a porous membrane having the above-mentioned pore diameter distribution by adjusting the type and amount of a solvent used in a stock solution for forming a membrane, and a drying method thereof after flow casting.

Manufacture of the porous membrane having pore diameter distribution can be carried out by a method including, for example, the following (1) to (4) in this order.

(1) A stock solution for fainting a membrane, which contains a polymer, if necessary an additive and, if necessary a solvent, is flow-cast on a support while being in a dissolved state.

(2) The surface of the flow-cast liquid membrane is exposed to temperature-controlled humid air.

(3) The membrane obtained after being exposed to temperature-controlled humid air is immersed in a coagulation liquid.

(4) A support is peeled off if necessary.

A temperature of temperature-controlled humid air may be 4° C. to 60° C., and is preferably 10° C. to 40° C. A relative humidity of the temperature-controlled humid air may be 20 to 95% RH, and is preferably 30 to 90% RH. The temperature-controlled humid air may be applied at a wind speed of 0.1 m/s to 10 m/s for 0.1 seconds to 30 seconds, preferably 1 second to 10 seconds.

In addition, an average pore diameter and position of the compact portion can also be controlled by a moisture concentration contained in the temperature-controlled humid air and a time of applying the temperature-controlled humid air. An average pore diameter of the compact portion can also be controlled by an amount of moisture contained in a stock solution for forming a membrane.

By applying the temperature-controlled humid air to the surface of the liquid membrane as described above, it is possible to cause coacervation from the surface of the liquid membrane toward the inside of the liquid membrane by controlling evaporation of a solvent. By immersing the membrane in a coagulation liquid containing a solvent having low solubility of the polymer but compatible with the solvent of the polymer in this state, the above-mentioned coacervation phase is fixed as fine pores, and pores other than the fine pores can also be formed.

A temperature of the coagulation liquid may be −10° C. to 80° C. in a process of immersing the membrane in the coagulation liquid. By changing a temperature during this period, it is possible to control a size of a pore diameter up to a support surface side by adjusting a time from the formation of the coacervation phase on the support surface side to the solidification from the compact portion. In a case where a temperature of the coagulation liquid is raised, the formation of the coacervation phase becomes faster and a time for solidification becomes longer, and therefore the pore diameter toward the support surface side tends to become large. On the other hand, in a case where a temperature of the coagulation liquid is lowered, the formation of the coacervation phase becomes slower and a time for solidification becomes shorter, and therefore the pore diameter toward the support surface side is unlikely to become large.

The porous membrane having pore diameter distribution is preferably manufactured using a stock solution for forming a membrane which contains a polymer selected from a group consisting of polysulfone and polyethersulfone, and is more preferably manufactured using a stock solution for forming a membrane which contains a polymer selected from the group consisting of polysulfone and polyethersulfone, and polyvinylpyrrolidone. In the stock solution for forming a membrane which is for manufacturing the porous membrane, a content of polyvinylpyrrolidone is preferably 50 mass % to 120 mass %, and is more preferably 80 mass % to 110 mass %, with respect to a total mass of polysulfone and polyethersulfone. Furthermore, in a case where the stock solution for forming a membrane contains lithium chloride as an additive, lithium chloride is preferably contained by an amount of 5 mass % to 20 mass %, and more preferably by 10 mass % to 15 mass %, with respect to the total mass of polysulfone and polyethersulfone.

As the coagulation liquid, it is preferable to use a solvent having a low solubility of the polymer used. Examples of such solvents include water, alcohols such as methanol, ethanol, and butanol; glycols such as ethylene glycol and diethylene glycol; aliphatic hydrocarbons such as ether, n-hexane, and n-heptane; glycerol such as glycerin; and the like. Examples of preferred coagulation liquids include water, alcohols, or a mixture of two or more of these. Among these, it is preferable to use water.

After immersion in the coagulation liquid, it is also preferable to perform washing with a solvent different from the coagulation liquid that has been used. Washing can be carried out by immersing in a solvent. Diethylene glycol is preferable as a washing solvent. Distribution of an N element in the porous membrane can be adjusted by adjusting either or both of a temperature and an immersion time of diethylene glycol in which a film is immersed by using diethylene glycol as a washing solvent. In particular, in a case where polyvinylpyrrolidone is used as the stock solution for forming a membrane of the porous membrane, a residual amount of polyvinylpyrrolidone on the membrane can be controlled. After washing with diethylene glycol, furthermore, the membrane may be washed with water.

Regarding a method for manufacturing the porous membrane having pore diameter distribution, reference can be made to JP1992-349927A (JP-H04-349927A), JP1992-068966B (JP-H04-068966B), JP1992-351645A (JP-H04-351645A), JP2010-235808A, and the like.

(Other Layers)

The membrane for immunoisolation may include other layers along with the porous membrane.

Examples of other layers include a hydrogel membrane. As a hydrogel membrane, a biocompatible hydrogel membrane is preferable. Examples thereof include an alginic acid gel membrane, an agarose gel membrane, a polyisopropyl acrylamide membrane, a membrane containing cellulose, a membrane containing a cellulose derivative (for example, methyl cellulose), a polyvinyl alcohol membrane, or the like. The hydrogel membrane is preferably an alginic acid gel membrane. Specific examples of alginic acid gel membranes include a polyion complex membrane of alginic acid-poly-L-lysine-alginic acid.

<Injection Port>

The chamber for transplantation preferably includes an injection port or the like for injecting the biological constituent or the like into the chamber for transplantation. As the injection port, a tube communicating with the inside of the chamber for transplantation may be provided.

The tube may contain a thermoplastic resin, for example. The thermoplastic resin preferably has a melting point which is lower than that of the polymer material of the porous membrane.

Specific examples of thermoplastic resins used in the tube include polyethylene, polypropylene, polyurethane, polyvinyl chloride, polytetrafluoroethylene, polyethylene terephthalate, polycarbonate, and the like. Among them, polyethylene, polypropylene, polyurethane, polyvinyl chloride, and polytetrafluoroethylene are preferable, and polyethylene, polyurethane, and polyvinyl chloride are particularly preferable.

For example, the tube is sandwiched between the membranes for immunoisolation in a manner of coming into contact with a part of the porous membrane, and thereby joining with the part thereof. Joining can be performed by fusion welding, adhesion using an adhesive, and the like. Among them, it is preferable to perform fusion welding. It is sufficient for the fusion welding to be heat fusion welding.

In a case of performing fusion welding, the tube preferably contains a thermoplastic resin having a melting point which is lower than that of the polymer material of the porous membrane. The reason is that, in a case of performing fusion welding between the porous membrane and a tube containing a thermoplastic resin having a melting point which is lower than that of the polymer material of the porous membrane, the tube material is considered first melted at the time of heating so that the melted tube material can get into the pores of the porous membrane.

In a case of performing adhesion, the adhesive can be appropriately selected according to the polymer constituting the membrane or the material of the tube, and it is possible to use epoxy-based adhesives, silicone-based adhesives, acrylic-based adhesives, urethane-based adhesives, and the like as the adhesive. For example, in a case where a tube containing a resin material having a melting point lower than that of the polymer material of the porous membrane is used, joining can be performed by adhesion.

<<Application of Chamber for Transplantation>>

The chamber for transplantation encloses the biological constituent and is used for transplantation of the biological constituent into the recipient. By using the chamber for transplantation, it is possible to prevent an immune rejection of the recipient with respect to the transplanted biological constituent. That is, the membrane for immunoisolation can be used for protecting biological constituents from an immune system of a recipient. In the present specification, a recipient means a living body to which transplantation is performed. A recipient is preferably a mammal and is more preferably a human.

<Biological Constituent>

The biological constituent means a structure body derived from a living body. Examples of living bodies include viruses, bacteria, yeasts, fungal cells, insects, plants, mammals, and the like. It is preferable that a living body be generally a mammal. Examples of mammals include bovines, swine, sheep, cats, dogs, humans, and the like. The biological constituent is preferably a structure body derived from any of mammals.

Examples of biological constituents include organs, tissues, cells, and the like. Among these, cells are preferable as biological constituents. As cells, a single cell may be used or a plurality of cells may be used. It is preferable that a plurality of cells be used. A plurality of cells may be separated from each other or may be an aggregate.

The biological constituent may be obtained directly from a living body. In addition, particularly in a case where the biological constituent is a cell, the biological constituent may be directly obtained from a living body, or may be obtained by differentiation-induction of cells such as embryonic stem cells (ES cell), induced pluripotent stem cells (iPS cell), and mesenchymal stem cells. The cell may be a progenitor cell.

As a biological constituent, as one aspect, it is preferable to release a physiologically active substance. Examples of physiologically active substances include various hormones, various cytokines, various enzymes, and various other biologic factors in a living body. More specific examples include insulin, dopamine, factor VIII, and the like.

Here, insulin is a polypeptide (molecular weight of about 6000) in which an A chain of 21 amino acid residues and a B chain of 30 amino acid residues are linked via a disulfide bond. In insulin in a living body of a mammal is secreted from β cells in pancreatic islets of Langerhans. In a case of using insulin-secreting cells as the biological constituent in the present invention, insulin secreted may be human-type insulin or other mammalian-type (for example, porcine-type) insulin. Insulin may be insulin produced by a genetic recombination method. As a method for obtaining genetically modified insulin, for example, the description of Kadowaki Takashita: Diabetes Navigator (refer to 270-271, Takeo Tao, Yoshikazu Oka "Insulin Preparations of Present and Future," Medical Review, 2002) can be referred to. Various types of insulin analogues (refer to, for example, H. C. Lee, J. W. Yoon, et al., Nature, 408, 483-488, 2000) may be used.

The biological constituent is preferably an insulin-secreting cell. Insulin-secreting cells are cells that can secrete insulin in response to changes in blood glucose level. The insulin-secreting cells are not particularly limited. Examples thereof include pancreatic β cells present in pancreatic islets of Langerhans. Pancreatic β cells may be human pancreatic β cells, or may be pancreatic β cells such as pigs and mice. For a method for extracting pancreatic β cells from a pig, reference can be made to the description in JP2007-195573A. In addition, the insulin-secreting cells may be cells derived from human stem cells (refer to, for example, Junichi Miyazaki, Regenerative Medicine, Vol. 1, No. 2, pp. 57-61, 2002), or cells derived from small intestinal epithelial stem cells (refer to, for example, Fumikomi Mineko et al., Regenerative Medicine, Volume 1, No. 2, pp. 63 to 68, 2002), or insulin-secretory cells into which a gene encoding insulin has been incorporated (refer to, for example, H. C. Lee, J. W. Yoon, et al., Nature, 408, pp. 483-488, 2000). Furthermore, the insulin-secreting cells may be pancreatic islets of Langerhans (refer to, for example, Horiyama, Kazumori Inoue, Regenerative Medicine, Volume 1, No. 2, pp. 69 to 77, 2002).

<Device for Transplantation>

The device for transplantation is a complex including at least a chamber for transplantation and a biological constituent. In the device for transplantation, the chamber for transplantation encloses the biological constituent therein.

In the device for transplantation, the chamber for transplantation may enclose only the biological constituent therein, or may enclose the biological constituent, and constituents or components other than the biological constituent therein. For example, the biological constituent may be enclosed in the chamber for transplantation together with a hydrogel, and preferably in a state of being enclosed in the hydrogel. In addition, the device for transplantation may contain pH buffers, inorganic salts, organic solvents, proteins such as albumin, or peptides.

The device for transplantation may contain only one biological constituent or may contain two or more biological constituents. For example, the device for transplantation may contain only a biological constituent which releases physiologically active substances for the purpose of transplantation, or which serves other functions of transplantation; or may further contain a biological constituent assisting functions of these biological constituents.

The device for transplantation may be, for example, a device to be transplanted intraperitoneally or subcutaneously. In addition, the device for transplantation may be a blood-vessel-connecting device. For example, in a case where insulin-secreting cells are used as the biological constituent, insulin secretion corresponding to a change in blood glucose level becomes possible by performing transplantation such that blood and the membrane for immunoisolation come into direct contact with each other.

Regarding the device for transplantation and chamber for transplantation, the description of Protein Nucleic Acid Enzyme, Vol. 45, pp. 2307 to 2312, (Okawara Hisako, 2000), JP2009-522269A, JP1994-507412A (JP-H06-507412A), and the like can be referred to.

EXAMPLES

Characteristics of the present invention will be described in more detail with reference to the following examples and comparative examples. The materials, amounts used, proportions, treatment details, treatment procedures, and the like disclosed in the following Examples can be modified as appropriate as long as the gist of the present invention is maintained. Therefore, the scope of the present invention should not be limitedly interpreted by the specific examples described below.

<Production of Porous Membrane>

Polysulfone Porous Membrane 15 parts by mass of polysulfone (P3500 manufactured by Solvay), 15 parts by mass of polyvinylpyrrolidone (K-30), 1 part by mass of lithium chloride, and 2 parts by mass of water were dissolved in 67 parts by mass of N-methyl-2-pyrrolidone. Thereby, a stock solution for forming a membrane was obtained. This stock solution for forming a membrane was flow-cast on a surface of a PET film. The flow-cast membrane surface was exposed to air adjusted to 30° C. and relative humidity 80% RH, at 2 m/sec for 5 seconds. Immediately thereafter, the film was immersed in a coagulation liquid tank filled with water at 65° C. PET was peeled off, and therefore a porous membrane was obtained. Thereafter, the obtained porous membrane was put into a diethylene glycol bath at 80° C. for 120 seconds, and then was thoroughly washed with pure water. Thereby, a porous membrane having a dry thickness of 50 μm of Example 1 was obtained.

In addition, membranes were produced in the same manner by controlling respective bubble point diameters and thicknesses of the porous membrane to values shown in Table 1 through adjustment of the thickness of the flow-cast stock solution for forming a membrane, an amount of water in the stock solution for forming a membrane, the temperature and relative humidity of temperature-controlled humid air after flow-cast, and the temperature of the coagulation liquid tank. Thereby, porous membranes of Examples 2 to 4, 9, and 10 were obtained.

Cellulose Acetate Porous Membrane 5 parts by mass of cellulose acetate (CA1; degree of substitution 2.9) was dissolved in 55 parts by mass of dimethyl chloride, and 34 parts by mass of methanol were added to the solution little by little. Next, 0.2 parts by mass of glycerin and 6 parts by mass of pure water were added to the solution little by little to obtain a solution with almost no undissolved material, and the solution was filtered with a filter paper. Thereby, a dope was prepared.

The prepared dope was sent by a gear pump, was filtered, and then was flow-cast from a die on a polyethylene terephthalate (PET) film which was transported on an endless band.

The flow-cast membrane was dried with a drying air at 20° C. to 40° C. for 20 minutes.

The film with PET was peeled off from the endless band, was dried with hot air at 80° C. to 120° C. for 15 minutes, and was wound with a winder. A number of fine holes were formed in the cellulose acetate on PET.

A fine porous membrane of the cellulose acetate was peeled off from PET using a peeling bar. Thereby, a porous membrane of Example 5 was obtained.

A porous membrane of Example 6 was obtained by producing a membrane in the same procedure as Example 5 except that cellulose acetate (degree of substitution 2.9) was replaced with another cellulose acetate (CA2; degree of substitution 2.5).

Cellulose Mixed Ester (CA Mixture) Porous Membrane 4 parts by mass of cellulose acetate (degree of substitution 2.5), 3 parts by mass of nitrocellulose, 23 parts by mass of dimethyl chloride, 22 parts by mass of acetone, 38 parts by mass of methanol, and 3.5 parts by mass of pure water were mixed and dissolved, and then the solution was filtered with a filter paper. Thereby, a dope was prepared.

The dope was flow-cast on a glass plate and was dried at 25° C. for 30 minutes. Subsequently, the membrane was dried at 65° C. for 10 minutes and peeled off from the glass plate. Thereby, a porous membrane of Example 7 was obtained.

PVDF Porous Membrane 15 parts by mass of polyvinylidene fluoride resin, 65 parts by mass of dimethylacetamide, and 20 parts by mass of polyethylene glycol were mixed, and then 1 part by mass of polyoxyethylene sorbitan monooleate was added to the solution. Thereby, a mixed solution was obtained. The mixed solution was flow-cast on a glass plate. The plate was immediately immersed in water at 65° C. for 3 minutes, washed with water at 20° C., and then dried.

Subsequently, the plate was immersed in an aqueous solution of 30 mass % sodium hydroxide at 40° C. for 20 minutes, washed with water at 20° C., and then dried. Thereby, a porous membrane of Example 8 was obtained.

PTFE Porous Membrane

A mixture in which 20 parts by mass of liquid lubricant (liquid paraffin) was added to 100 parts by mass of PTFE powder was premolded and molded into a round bar by a paste extrusion. The PTFE molded product was rolled to have a thickness of 0.2 mm, the liquid lubricant was removed using an extraction solvent (decane), and then the extraction solvent was removed using a dryer heated to 150° C. Thereby, a PTFE sheet was obtained.

The obtained sheet was stretched approximately 5 times in the width direction (first stretching) and then stretched simultaneously in the biaxial direction (second stretching) using a biaxial stretching machine under the conditions of a stretching temperature of 300° C. and a stretching rate of 50%/sec. In the second stretching, the obtained sheet was stretched 7 times in each of two directions at a rate of 50%/sec. After stretching, the sheet was baked by heating at 380° C. for 10 minutes in a state where the membrane dimensions were fixed. Thereby, membranes of Comparative Examples 1 and 3 were obtained.

PET Porous Membrane

A biaxially stretched PET film having a desired heat shrinkage percentage was obtained by changing a heat fixation temperature by a method described in Example 1 of JP2011-208125A.

The film was irradiated with an argon ion beam such that an incidence angle was perpendicular to the main surface of the film. The irradiation density of argon ion was set to $2.0 \times 10^7$ per 1 $cm^2$. The irradiated film was immersed in an etching treatment liquid for 1 minute (an aqueous solution of 40 mass % of an ethanol concentration and 14 mass % of a potassium hydroxide concentration) which was kept at 60° C. Thereafter, the film was taken out from the etching treatment liquid, was immersed in pure water at 60° C. for 10 minutes to be washed, and then stored in a drying oven at 30° C. for 60 minutes to be dried. Thereby, a membrane of Comparative Example 2 was obtained.

<Evaluation of Porous Membrane>

Bubble Point Diameter Evaluation

In a pore diameter distribution measurement test using a permporometer (CFE-1200AEX manufactured by SEIKA CORPORATION), a bubble point diameter of a membrane sample completely wetted by GALWICK (manufactured by PorousMaterials, Inc.) was evaluated after increasing an air pressure at 5 $cm^3$/min.

Membrane Thickness

A cross section of the membrane was observed by computer tomography (CT), and an average thickness value at five locations was evaluated.

Porosity

A porosity was evaluated by a value calculated by the following formula.

$$\text{Porosity (\%)} = [1 - \{m/\rho/(S \times d)\}] \times 100$$

m: Mass of porous membrane (g)
ρ: Polymer density (g/$cm^3$)
S: Area of porous membrane ($cm^2$)
d: Thickness of porous membrane (cm)

As the polymer density, 1.24 was used for the polysulfone porous membrane, 1.27 was used for the cellulose acetate porous membrane (CA1, CA2), 1.33 was used for the cellulose mixed ester (CA mixture) porous membrane, 2.17 was used for the PTFE porous membrane, and 1.37 was used for the PET porous membrane.

Flexibility

The produced porous membrane was cut into a 10×30 mm rectangle. Under the conditions of 25° C. and a relative humidity of 60%, a portion of 10 mm from a surface side (edge) of one short side was vertically sandwiched between flat plates while not bending the membrane, and the flat plates were placed horizontally. A distance between a horizontal plane including a center plane in a thickness direction of the sandwiched portion of the porous membrane, and a part, which was farthest from the horizontal plane, of a residual 20 mm-length portion of the porous membrane which was in a free state and projected from the flat plate, was defined as flexibility.

<Production and Evaluation of Chamber for Transplantation>

Production of Chamber for Transplantation

Two sheets were cut out from the produced membrane, and these two sheets were laminated. In Examples 1 to 8, two sheets were laminated so that surfaces on a side opposite to the support were facing each other at the time of manufacture. An end portion of these porous membranes was sandwiched by a polyethylene spacer having a width of 1 mm and a thickness of 1.3 mm. The end portion was sandwiched by the spacer so the joint portion continued in a square shape as shown in FIG. 1. The peripheral portions (outer periphery) in which the spacers were provided were joined by an impulse heat sealer while not joining a part thereof. Thereby, a bag-shaped chamber for transplantation was produced (FIG. 1). The chamber for transplantation was produced such that the outermost dimensions of a non-joint portion of the porous membrane was as shown in Table 1.

Figure 2:
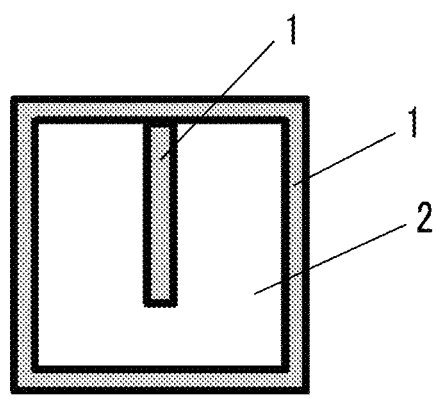
FIG. 2 is a view showing a joint portion in a chamber for transplantation of Comparative Example 3.

Regarding Comparative Example 3, a partition having a length of 15 mm was provided vertically from the center of one side among the four sides toward the inside of the chamber for transplantation. As shown in FIG. 2, polyethylene spacers having a width of 1 mm and a thickness of 1.3 mm were continuously provided at the peripheral portions (outer periphery) and the partition, and then portions in which the spacers were provided were joined by an impulse heat sealer while not joining a part of the edge part. Thereby, a chamber for transplantation having a joint portion as a partition in an interior space was produced.

As Comparative Example 4, a chamber for transplantation described in pages 17 and 18 of JP1996-507950A (JP-H08-507950A) was produced and evaluated.

Table 1 shows a distance between the shape of the chamber for transplantation to a point farthest from any position of the joint portion in the membrane surface.

Shortest Distance Between Membranes

The cross section of the produced chamber for transplantation was observed by CT. The shortest distance between two joined membranes was measured and evaluated in three grade.
1: 0.7 mm or longer
2: longer than 0 mm and shorter than 0.7 mm
3: 0 mm (in contact)

Maximum Cross-Sectional Area

A cross section image was extracted from the CT observation, and a value at which an area surrounded by the joint portion became maximum was obtained.

Space Volume

A volume of the interior space was calculated from the CT observation and was evaluated in three grade.
1: 360 mm$^3$ or more
2: 200 mm$^3$ or more and less than 360 mm$^3$
3: less than 200 mm$^3$ Embedding Evaluation Islet cells were prepared using an islet culture kit (rat) manufactured by Cosmo Bio.

Two porous membranes were allowed to face each other, polyethylene spacers having a thickness of 1.5 mm were sandwiched between the membranes, and the peripheral portions were joined by an impulse heat sealer while not joining a part thereof. Thereby, a bag-shaped chamber for transplantation was produced. The produced chamber for transplantation was sterilized with ethylene oxide gas, the islet cells were inserted in the bag from unjoined portions, and then the chamber was sealed by joining the unjoined portions. In Comparative Example 4, only one-fourth the number of islet cells encapsulated in Examples 1 to 8 and Comparative Examples 1 to 3 could be encapsulated.

The chamber for transplantation in which the islet cells were encapsulated was transplanted into a rat and removed after 2 weeks, and then changes in an amount of insulin released in response to glucose were evaluated.

(Change in response amount)=(Response amount after 2 weeks)/(Response amount before encapsulation)×100%

1: 75% or more
2: 60% or more and less than 75%
3: 45% or more and less than 60%
4: less than 45%

The results are shown in Table 1.

TABLE 1

| | | Membrane physical properties | | | | | | Evaluation of chamber for transplantation | | | | | | |
| | | | | | | | | | | Distance to a point farthest | | | | |
| | Polymer | Bubble point diameter μm | Thickness μm | Porosity | Flexibility mm | Dimensions mm × mm | Joint portion | Maximum cross-sectional area cm$^2$ | from joint portion in surface Mm | Shortest distance between membranes | | Space volume | | Embedding evaluation |
| Example 1 | PSf | 1.5 | 50 | 76% | 8.0 | 22 × 22 | Only peripheral portion | 4 | 10 | 1 | 0.81 | 1 | 375 | 1 | 85% |
| Example 2 | PSf | 1 | 35 | 82% | 8.2 | 22 × 22 | Only peripheral portion | 4 | 10 | 1 | 0.79 | 1 | 372 | 1 | 88% |
| Example 3 | PSf | 0.6 | 25 | 75% | 8.1 | 22 × 22 | Only peripheral portion | 4 | 10 | 1 | 0.80 | 1 | 373 | 1 | 83% |
| Example 4 | PSf | 1.2 | 200 | 81% | 5.5 | 22 × 22 | Only peripheral portion | 4 | 10 | 1 | 0.86 | 1 | 382 | 1 | 75% |
| Example 5 | CA1 | 1 | 80 | 87% | 1.1 | 22 × 22 | Only peripheral portion | 4 | 10 | 1 | 0.97 | 1 | 396 | 3 | 57% |
| Example 6 | CA2 | 1 | 80 | 80% | 1.2 | 22 × 22 | Only peripheral portion | 4 | 10 | 1 | 0.97 | 1 | 396 | 3 | 54% |
| Example 7 | CA mixture | 0.06 | 150 | 73% | 4.0 | 22 × 22 | Only peripheral portion | 4 | 10 | 1 | 0.90 | 1 | 387 | 2 | 70% |
| Example 8 | PVDF | 0.6 | 115 | 40% | 1.6 | 22 × 22 | Only peripheral portion | 4 | 10 | 1 | 0.96 | 1 | 395 | 3 | 49% |
| Example 9 | PSf | 1 | 35 | 82% | 8.2 | 42 × 52 | Only peripheral portion | 20 | 20 | 1 | 0.72 | 1 | 1804 | 1 | 84% |
| Example 10 | PSf | 1 | 35 | 82% | 8.2 | 62 × 86 | Only peripheral portion | 50 | 30 | 2 | 0.68 | 1 | 4440 | 1 | 82% |
| Comparative Example 1 | PTFE | 0.55 | 22 | 30% | 18.0 | 22 × 22 | Only peripheral Portion | 4 | 10 | 3 | 0.00 | 2 | 200 | 4 | 30% |

TABLE 1-continued

| | | Membrane physical properties | | | | | | Evaluation of chamber for transplantation | | | | |
| | | | | | | | | | Distance to a point farthest | | | |
| | Polymer | Bubble point diameter μm | Thickness μm | Porosity | Flexibility mm | Dimensions mm × mm | Joint portion | Maximum cross-sectional area cm² | from joint portion in surface Mm | Shortest distance between membranes | Space volume | Embedding evaluation |
|---|---|---|---|---|---|---|---|---|---|---|---|---|
| Comparative Example 2 | PET | 1 | 24 | 17% | 13.1 | 22 × 22 | Only peripheral portion | 4 | 10 | 2 0.44 | 2 288 | 4 37% |
| Comparative Example 3 | PTFE | 0.55 | 22 | 30% | 18.0 | 23 × 23 | Peripheral portion + Partition | 4 | 4.5 | 2 0.25 | 2 249 | 4 34% |
| Comparative Example 4 | PTFE | 0.55 | 24 | 30% | 18.0 | 28 × 6 | Only peripheral portion | 1.3 | 2.5 | 2 0.00 | 3 75 | 4 28% |

Psf: Polysulfone; CA: Cellulose acetate; PVDF: Polyvinylidene fluoride; PTFE: Polytetrafluoroethylene; PET: Polyethylene terephthalate

EXPLANATION OF REFERENCES

1: joint portion
2: non-joint portion

What is claimed is:

1. A chamber for transplantation, comprising:
a membrane for immunoisolation at a boundary between an inside and an outside of the chamber for transplantation,
wherein the membranes for immunoisolation face each other to form an interior space,
the membranes for immunoisolation which face each other have joint portions that are joined to each other,
the interior space includes a point at a distance of 10 mm or longer from any position of the joint portion, and
the membrane for immunoisolation has flexibility that allows a distance of 1 mm to 13 mm as the following distance, measured as follows:
a portion of 10 mm from a side surface of one short side of a 10 mm×30 mm rectangular test piece of the membrane for immunoisolation is vertically sandwiched between flat plates,
the flat plates are placed horizontally, and
a distance between a horizontal plane including a center plane in a thickness direction of the sandwiched portion of the membrane for immunoisolation, and a part, which is farthest from the horizontal plane, of a residual 20 mm-portion projecting from the flat plate is measured.

2. The chamber for transplantation according to claim 1, wherein a maximum cross-sectional area of the interior space is 4 cm² to 200 cm².

3. The chamber for transplantation according to claim 1, wherein the joint portions are at end portions of the membranes for immunoisolation which face each other.

4. The chamber for transplantation according to claim 1, wherein the joint portions are only at end portions of the membranes for immunoisolation which face each other.

5. The chamber for transplantation according to claim 1, wherein the membrane for immunoisolation includes a porous membrane containing a polymer.

6. The chamber for transplantation according to claim 5, wherein a thickness of the porous membrane is 25 μm to 250 μm.

7. The chamber for transplantation according to claim 5, wherein a porosity of the porous membrane is 35% to 90%.

8. The chamber for transplantation according to claim 5, wherein the porous membrane contains polysulfone or polyethersulfone.

9. The chamber for transplantation according to claim 1, wherein the membrane for immunoisolation is formed of a porous membrane containing a polymer.

* * * * *